United States Patent [19]
Hayden et al.

[11] Patent Number: 5,658,729
[45] Date of Patent: Aug. 19, 1997

[54] METHOD, REAGENT AND KIT FOR EVALUATING SUSCEPTIBILITY TO PREMATURE ATHEROSCLEROSIS

[75] Inventors: Michael R. Hayden, Vancouver, Canada; Yuanhong Ma, Los Altos, Calif.; Suzanne Lewis, West Vancouver; Guoquing Liu, Vancouver, both of Canada

[73] Assignee: The University of British Columbia, Vancouver, Canada

[21] Appl. No.: 320,604

[22] Filed: Oct. 11, 1994

[51] Int. Cl.$^6$ .............. C07H 21/04; C12P 19/34; C12Q 1/68
[52] U.S. Cl. .............. 435/6; 435/91.1; 435/91.2; 435/810; 536/23.2; 536/24.3; 536/24.31; 536/24.33; 536/24.5
[58] Field of Search .............. 435/6, 91.1, 91.2, 435/810; 536/23.2, 24.3, 24.31, 24.33, 24.5

[56] References Cited

U.S. PATENT DOCUMENTS

| | | | |
|---|---|---|---|
| 4,683,195 | 7/1987 | Mullis et al. | 435/61 |
| 4,683,202 | 7/1987 | Mullis | 435/91 |
| 4,957,858 | 9/1990 | Chu et al. | 435/6 |
| 5,124,246 | 6/1992 | Urdea et al. | 435/6 |
| 5,200,314 | 4/1993 | Urdea | 435/6 |
| 5,270,184 | 12/1993 | Walker et al. | 435/91.2 |

FOREIGN PATENT DOCUMENTS

| | | |
|---|---|---|
| 0497272 | 8/1992 | European Pat. Off. . |
| 2202328 | 9/1988 | United Kingdom . |
| 89/09284 | 10/1989 | WIPO . |

OTHER PUBLICATIONS

Normand et al. Human Genetics 89:671–675, 1992.
Hayden et al., "Molecular genetics of Human Lipoprotein Lipase Deficiency", *Molecular and Cellualr Biochemistry* 113: 171–176 (1992).
Ma et al., "High Frequency of Mutation in the Human Lipoprotein Lipase Gene in Pregancy–Induced Chylomicronemia: Possible Association with Apoplipoprotein E2 Isoform", *J. Lipid Research* 35: 1066–1075 (1994).
Ma et al., "Type III Hyperlipoproteinemia in Apo E2/2 Homozygotes: Possible Role of Mutations in the Lipoprotein Lipase Gene", *Circulation, Abstracts from the 66th Scientific Session of American Heart Association* 1–179 (1993).
Gordon et al., "High Density Lipoprotein As a Protective Factor Against Coronary Heart Disease" *The Amer. J. Med.* 62: 707–714 (1977).
Hobbs, et al, "Molecular Genetics of the LDL Receptor Gene in Familial Hypercholesterolemia", *Human Mutations* 1: 445–466 (1992).

(List continued on next page.)

Primary Examiner—Stephanie W. Zitomer
Assistant Examiner—Paul B. Tran
Attorney, Agent, or Firm—Oppedahl & Larson

[57] ABSTRACT

A single point mutation in the human lipoprotein lipase gene which results in an A→G nucleotide change at codon 291 (nucleotide 1127) of the lipoprotein lipase gene, and a substitution of serine for the normal asparagine in the lipoprotein lipase gene product is seen with increased frequency in patients with coronary artery disease, and is associated with an increased susceptibility to coronary artery disease, including in particular premature atherosclerosis. This is expressed as a diminished catalytic activity of lipoprotein lipase, lower HDL-cholesterol levels and higher triglyceride levels. Thus, susceptibility of a human individual to premature atherosclerosis and other forms of coronary artery disease can be evaluated by evaluating the sample of DNA for the presence of nucleotides encoding a serine residue as amino acid 291 of the lipoprotein lipase gene product. The presence of a serine residue is indicative of increased susceptibility in the patient. This method may be performed using a kit which contains a pair of primers selected to amplify a region of a human lipoprotein lipase gene spanning amino acid 291 of human lipoprotein lipase.

39 Claims, 2 Drawing Sheets

OTHER PUBLICATIONS

Soria et al., "Association between a specific apolipoprotein B mutation and familial defective apolipoprotein B-100", *Proc. Nat'l Acad. Sci. USA* 86: 587–91 (1989).

Brown et al., "Molecular Basis of Lipid Transfer Protein Deficiency in a Family With Increased High–Density Lipoproteins", *Nature* 342: 448–451 (1989).

Rubin et al., "Inhibition of Early Atherogenesis in Transgenic Mice by Human Apolipoprotein A1", *Nature* 353: 265–266 (1991).

Mullenbach et al. "An efficient salt–chloroform extraction of DNA from blood and tissues", *Trend in Genetics* 5: 391 (1989).

Oka et al., "Structure and polymorphic map of human lipoprotein lipase gene", *Biochim. Biophys. Acta* 1049: 21–26 (1990).

Deeb et al., "Structure of the Human Lipoprotein LIpase Gene", *Biochemistry* 28: 4131–4135 (1989).

Wion et al, "Human Lipoprotein Lipase Complementary DNA Sequence", *Science* 235: 1638–1641 (1987).

Monsalve et al., "A Missense Mutation at Codon 188 of the Human Lipoprotein LIpase Gene is a Frequent Cause of Lipoprotein Lipase Deficiency in Persons of Different Ancestories", *J. Clin. Invest.* 86: 728–734 (1990).

Stratford–Perricaudet et al., "Widespread Long–Term Gene Transfer to Mouse Skeletal Muscles and Heart", *J. Clin. Invest.* 90: 626–630 (1992).

Mulligan et al., "Expression of a Bacterials Gene in Mammalian Cells", *Science* 209: 1422–1427 (1980).

Liu, et al., "Alteration of Lipid Profiles in PLasma of Transgenic Mice Expressing Human Lipoprotein Lipase", *J. Biol. Chem.* 269: 11417–11424 (1994).

Tsutsumi et al., "The Novel Compound NO–1886 Increase Lipoproteim Lipase Activity with Resulting Elevation of High Density Lipoprotein Cholesterol, and Long–term Administration Inhibits Atherogenesis in the Coronary Arteries of Rats with Experimental Atherosclerosis", *J. Clin. Invest.* 92: 411–417 (1992).

Kuusi et al., "Postheparin plasma lipoprotein and hepatic lipase are determinants of hypo– and hyperalphalipoproteinemia", J. Lipid Research 30: .

Taskinen et al., "High Density lipoprotein subfractions in relation to lipoprotein lipase acticity of tissues in man—evidence of reciprocal regulation of HDL2 and HDL3 levels by lipoprotein lipase", *Clinica Chimica Acta* 112: 325–332 (1981).

Zilversmit, D.B., "A Proposal Linking Atherogenesis to the Interaction of Endothelial Lipoprotein LIpase with Triglyceride–Rich Lipoproteins", *Circulation Research* 33: 633–638 (1973).

FIG. 2

----PROBE W/DETECTABLE LABEL----

----AMPLIFIED GENE FRAGMENT----

----PROBE W/IMMOBILIZABLE LABEL----

MISMATCH METHOD

NORMAL GENE

```
              nt.1127              nt.1130
5'---A T C A A T A A A G T C---3'
3'---A          T G T C A G---5'
                  ↑
              MISMATCH
               PRIMER
```
↓ PCR, 30–35 CYCLES

```
    nt.1127                nt.1130
5'---A T C|A A T A C A|G T C---3'
3'---T A G|T T A T G T|C A G---5'
```
↓ RSA I DIGESTION

NO DIGESTION
1 FRAGMENT

ASN291SER MUTANT GENE

```
              nt.1127              nt.1130
5'---A T C A G T A A A G T C---3'
3'---A          T G T C A G---5'
                  ↑
              MISMATCH
               PRIMER
```
↓ PCR, 30–35 CYCLES

```
    nt.1127                nt.1130
5'---A T C|A G T A C A|G T C---3'
3'---T A G|T C A T G T|C A G---5'
```
↓ RSA I DIGESTION

2 FRAGMENTS

FIG. 3

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: no ( v i ) ORIGINAL SOURCE:
        ( A ) ORGANISM: human ( i x ) FEATURE: Primer for exon 6 of human LPL ( x i ) SEQUENCE DESCRIPTION: SEQ ID NO:1:

GCCGAGATAC AATCTTGGTG        20

( 2 ) INFORMATION FOR SEQ ID NO:2:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: no ( i v ) ANTI-SENSE: yes ( v i ) ORIGINAL SOURCE:
    ( A ) ORGANISM: human ( i x ) FEATURE: Mismatch primer for exon 6 of human LPL ( x i ) SEQUENCE DESCRIPTION: SEQ ID NO:2:

CTGCTTCTTT TGGCTCTGAC TGTA    24

( 2 ) INFORMATION FOR SEQ ID NO:3:

( i ) SEQUENCE CHARACTERISTICS:
        ( A ) LENGTH: 15
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v i ) ORIGINAL SOURCE:
        ( A ) ORGANISM: human ( i x ) FEATURE: internal fragment from normal human LPL gene spanning
            amino acid 291

( x i ) SEQUENCE DESCRIPTION: SEQ ID NO:3:

GAGATCAATA AAGTC    15

( 2 ) INFORMATION FOR SEQ ID NO:4:

( i ) SEQUENCE CHARACTERISTICS:
        ( A ) LENGTH: 15
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v i ) ORIGINAL SOURCE:
        ( A ) ORGANISM: human ( i x ) FEATURE: internal fragment from Asn291Ser mutant human LPL gene
            spanning amino acid 291

( x i ) SEQUENCE DESCRIPTION: SEQ ID NO:4:

GAGATCAGTA AAGTC    15

METHOD, REAGENT AND KIT FOR EVALUATING SUSCEPTIBILITY TO PREMATURE ATHEROSCLEROSIS

BACKGROUND OF THE INVENTION

This application relates to a method, reagent and kit for evaluating susceptibility to and causation of premature atherosclerosis and other forms of coronary artery disease. The invention further relates to a method of gene therapy by which lipoprotein lipase deficiencies can be treated, and to transducing vectors for use in such a method.

"Coronary artery disease" is a collective term for a variety of symptomatic conditions including angina, myocardial infarction, and non-specific chest, arm and face pain, which result from atherosclerosis of the arteries that supply blood to the heart. Atherosclerosis, commonly known as "hardening of the arteries" is caused by the formation of deposits of fatty substances such as cholesterol within the inner layers or endothelium of the arteries.

"Premature atherosclerosis" as used herein refers to the clinical presentation of signs and symptoms of coronary artery disease before the age of 65.

Because of the significant relationship between coronary artery disease and heart attacks, considerable effort has been devoted to identifying the biochemical causes of atherosclerosis. This research has shown that high levels of total cholesterol, low density lipoprotein (LDL), very low density lipoprotein (VLDL) and triglycerides are associated with increased risk of coronary artery disease, while high levels of high density lipoproteins (HDL) are associated with decreased risk of coronary artery disease. See, Gordon et al., *The Amer. J. Med.* 62: 707-714 (1977). However, while observation of lipoproteins, cholesterol and triglycerides can provide a basis for identifying individuals at risk of coronary artery disease, the levels of these substances are themselves symptoms of an underlying biochemical defect which remains unidentified. Thus, specific treatment of the ultimate cause rather than an intermeditate condition, and prediction of risk prior to the onset of this intermediate condition is not possible through such observation.

Studies directed towards the underlying cause of coronary artery disease have identified a number of mutations in genes coding for proteins involved in lipid transport and metabolism that appear to be associated with an increased risk. Examples include a large number of mutations in the low-density lipoprotein receptor gene, Hobbs et al., *Human Mutations* 1: 445-466 (1992), and a single mutation in the apolipoprotein-B (Apo-B) gene which underlies familial defective Apo-B in many parts of the world. Soria et al., *Proc. Nat'l Acad. Sci. USA* 86: 587-91 (1989). In addition, mutations in other genes which play a significant role in HDL metabolism such as the cholesterol ester transferase protein (CETP) gene, Brown et al., *Nature* 342: 448-451 (1989) and the gene for Apo-A1, Rubin et al., *Nature* 353: 265-266 (1991), have also been shown to be associated with either enhanced resistance or increased susceptibility to atherosclerosis. However, these mutations are uncommon and thus far no specific mutation in any gene has been found in a significant number (i.e., >1%) of patients with coronary artery disease or premature atherosclerosis. Accordingly, these test results while interesting do not offer the opportunity to provide evaluation or therapy to significant numbers of patients.

SUMMARY OF THE INVENTION

It has now been found that a single point mutation in the human lipoprotein lipase gene which results in an A→G nucleotide change at codon 291 (nucleotide 1127) of the lipoprotein lipase gene, and a substitution of serine for the normal asparagine in the lipoprotein lipase gene product is seen with increased frequency in patients with coronary artery disease, and is associated with an increased susceptibility to coronary artery disease, including in particular premature atherosclerosis. This is expressed as a diminished catalytic activity of lipoprotein lipase, lower HDL-cholesterol levels and higher triglyceride levels. Thus, in accordance with the present invention there is provided a method for evaluating susceptibility of a human individual to premature atherosclerosis and other forms of coronary artery disease comprising the steps of:

(a) obtaining a sample of DNA from the individual; and
(b) evaluating the sample of DNA for the presence of nucleotides encoding a serine residue as amino acid 291 of the lipoprotein lipase gene product. The presence of a serine residue is indicative of increased susceptibility in the patient.

The invention further provides a kit for performing the method of the invention. Such a kit comprises a pair of primers selected to amplify a region of a human lipoprotein lipase gene spanning amino acid 291 of human lipoprotein lipase. Appropriate additional reagents may also be included in the kit such as polymerase enzymes, nucleoside stock solutions and the like.

A further aspect of the present invention is a method of treating patients suffering from or likely to suffer from premature atherosclerosis and other forms of coronary artery disease as a result of a lipoprotein lipase deficiency using gene therapy. This may be accomplished using adenovirus-mediated or retrovirus-mediated gene therapy, and can be performed using either an in vivo or an ex vivo approach.

BRIEF DESCRIPTION OF THE DRAWINGS

FIG. 2 shows the sandwich formed when two oligonucleotide probes are used to analyze for the presence of an Asn291Ser mutation;

FIG. 3 illustrates the use of mismatch primers in accordance with the invention to detect the Asn291Ser mutation.

DETAILED DESCRIPTION OF THE INVENTION

The present invention involves the detection of a mutation in the gene coding for the enzyme lipoprotein lipase in a sample of DNA obtained from a patient.

The first step in the method in accordance with the invention is obtaining an appropriate sample of DNA. A suitable source of such a sample is from patient blood. Isolation of the DNA from the blood can be performed by many different methods. For example, the DNA may be isolated from the leukocytes using a salt-chloroformextraction as described in *Trends in Genetics* 5: 391 (1989).

Once the sample of patient DNA is obtained, it may be desirable to amplify a portion of the DNA including the region of interest. One technique which can be used for amplification is Polymerase Chain Reaction (PCR) amplification. This technique, which is described in U.S. Pat. Nos. 4,683,202 and 4,683,195, which are incorporated herein by reference, makes use of two amplification primers each of which hybridizes to a different one of the two strands of the DNA duplex at regions which do not overlap the site of the mutation being tested for, in this case the mutation in amino acid 291. Multiple cycles of primer extension, and denaturation are used to produce additional copies of DNA to which the primers can hybridize. This amplification can be performed in a solution, or on a solid support (see, e.g. U.S. Pat. No. 5,200,314 which is incorporated herein by reference).

The mutation site of interest is at a defined location within exon 6 of the lipoprotein lipase gene, the sequence of which is known in the art. Oka et al., *Biochim. Biophys. Acta* 1049: 21–26 (1990); Deeb et al., *Biochemistry* 28: 4131–4135 (1989); Wion et al., *Science* 235: 1638–1641 (1987). Amplification primers may be used which bind to the intron regions on either side of exon 6, or which bind to portions of exon 6 itself. Where amplification of the mutation site is desired, the primers should not overlap the site of the mutation of interest. Suitable primers include those described for exon 6 in Monsalve et al., *J. Clin. Invest.* 86: 728–734 (1990).

Figure 1:
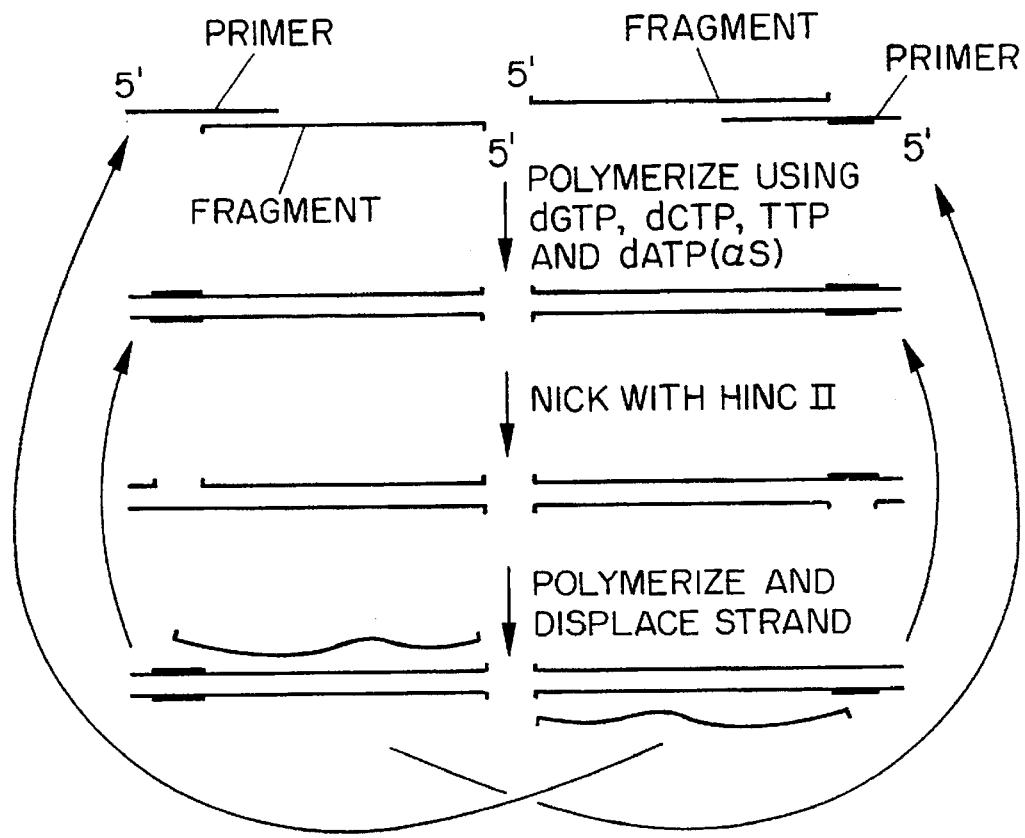
FIG. 1 illustrates the use of strand displacement amplification in a method in accordance with the present invention.

Another amplification technique which may be used in accordance with the present invention is known as Strand Displacement Amplification (SDA). In this technique, which is described in U.S. Pat. No. 5,270,184, incorporated herein by reference, and EP 0 497 272, and which is exemplified in FIG. 1, a gene fragment is used as the target, and a primer is used which binds to the 3'-end of this fragment. The primer is selected to include a restriction site near its 5'-end. This can be achieved by using a primer which extends beyond the 3'-end of the target gene fragment if there is no restriction site conveniently located towards the 3'-end of the fragment from the site of interest. The primer and the target fragment (if the primer extends beyond the end of the fragment) are extended to form a duplex using modified nucleoside feedstocks, e.g., α-thio nucleoside triphosphates, at least in the region of the restriction cleavage site so that the newly formed strand is not susceptible to cleavage by the endonuclease. For subsequent amplification normal feedstocks are used. A restriction endonuclease is introduced which nicks the duplex at the restriction site. Extension then starts over at the site of the nick, at the same time that the previously hybridized oligonucleotide is displaced. In this way, multiple copies of one or both strands of a gene or gene fragment can be amplified without the use of temperature cycling.

To use strand displacement amplification to amplify the mutation site responsible for the Asn291Ser mutation, primers flanking exon 6, such as those described in Mortsalve et al. could be used.

Once amplified, the DNA may be evaluated by any of a number of methods to determine if the Asn291Ser mutation is present. First, the amplified DNA can be sequenced (optionally after cloning into a TA cloning vector, available from Invitrogen, Inc.) using manual or automated sequencing of the amplified product. Since the complete sequence of exon 6 of normal lipoprotein lipase is known, targeted sequencing primers can be readily developed for this purpose.

Another approach to the detection of Asn291Ser mutations, generally used following amplification, is the use of sequence specific oligonucleotide probes which bind to one of the mutant or wildtype form, but not to the other. Such probes generally have a length of 15 to 20 bases. Because the difference being evaluated is a single base, the analysis is conducted under very stringent hybridization conditions such that only perfect matches will form stable hybrids.

The probe used in the invention is advantageously labeled to permit its easy detection. Suitable labels include radioactive labels, fluorescent labels, and reactive labels such as biotin. The probe may also be labeled twice, for example with a radiolabel and a reactive label, in which case the reactive label may be used to the capture the DNA hybrid, for example through the reaction of biotin with an avidin-coated support.

A preferred format for testing using sequence specific probes involves the use of a sandwich assay in which the amplified DNA is evaluated using two probes. The first oligonucleotide probe is either selected to bind specifically to a gene encoding a mutant human lipoprotein lipase having a serine residue as amino acid 291, wherein said probe binds to a portion of the gene including the bases coding for the serine residue or selected to bind specifically to a gene encoding a normal human lipoprotein lipase having an asparagine residue as amino acid 291, wherein said probe binds to a portion of the gene including the bases coding for the asparagine residue. The second oligonucleotide probe is selected to bind to a different, non-overlapping portion of the human-LPL gene which is the same in both mutant and non-mutant forms. One of the two probes is labeled with a detectable label while the other is labeled with a reactive label to facilitate immobilization. Only when both probes are bound to a single piece of amplified DNA will the detectable label be immobilized through the formation of a sandwich of the structure shown in FIG. 2.

Various modifications of the amplification process may also be used in accordance with the present invention to detect the presence of an Asn291Ser mutation. If intentionally mismatched primers are used during the amplification, the amplified nucleic acids may also be evaluated for the presence of the Asn291Ser mutation using a technique called restriction fragment length polymorphism (RFLP). In order to make use of RFLP directly to detect a point mutation (as opposed to an insertion or deletion mutation), the mutation must result in the addition or loss of a site cleaved by a restriction endonuclease. If this is the case, the fragments produced upon restriction endonuclease digestion of the normal and mutant gene differ in number, in size, or in both. This difference can be detected by gel electrophoresis of the restriction fragments.

In the case of the Asn291Ser mutation, the nucleotide sequence of the coding strand changes from 5'- - - - - -GAC ATC AAT AAA GTC - - - - - - 3' (SEQ ID NO.: 3)
to
5'- - - - -GAG ATC AGT AAA GTC - - - - - - 3' (SEQ ID NO.: 4)

These fragments lack the two-fold symmetry that is associated with cleavage sites of restriction endonucleases, and thus one cannot simply use an enzyme which will cleave one of the sequences but not the other. RFLP can be used, however, if a special mismatch primer is used during the amplification process. This primer, shown below in Example 1, binds to the LPL gene at a site adjacent to the mutation of interest, and introduces an intentional error into the amplified DNA. Thus, as illustrated in FIG. 3, instead of the expected sequence, the mismatch primer produces the duplex region 5'- - -ATAC- - -3' coding strand
3'- - -TATG- - -5' non-coding strand -continued when a wild-type gene is amplified, and the sequence
5'- - -GTAC- - -3' coding strand
3'- - -CATG- - -5' non-coding strand when a mutant gene is amplified, where the C/G pair in the fourth position of the above fragments is the intentional mismatch. Amplified mutant genes therefore contain a restriction site (5'-GTAC-3') which is cleaved by the restriction endonuclease RsaI, but amplified wild-type sequence (5'-ATAC-3') does not. Thus, a polymorphism measurable through restriction fragment lengths is artificially introduced into the amplified DNA using the mismatch primers.

The amplification process may also be modified by using labeled primers which facilitate detection and/or capture of the amplified product. For example, as described in British Patent No. 2 202 328, using a biotin-labeled primer as one of the two primers permits the recovery of the extended primers produced during the amplification reaction, e.g., by binding the extended primers to a support coated with (strept)avidin. If the primer used is in a region flanking the mutation site, the presence of the mutation can be detected by adding a labeled probe, which specifically binds to the mutant or wild-type gene, to the biotinylated amplified DNA either before or after capture of the amplified DNA on a support. If the label becomes bound to the support, this indicates that the probe was bound. Alternatively, the primer may be one which spans the mutation site in which case amplification will occur using a primer corresponding to the mutant sequence only when the mutation is present (and vice versa). In this case, a labeled probe which binds to a portion of the LPL gene away from the mutation site or labeled nucleoside feedstocks may be used to introduce a label into the amplified DNA.

The presence of the Asn291Ser mutation may also be detected using a catalytic hybridization amplification system of the type described in International Patent Publication No. WO89/09284, which is incorporated herein by reference. Basically, in this technique, the target nucleic acid acts as a cofactor for enzymatic cleavage of probe oligonucleotides. Thus, a substantial excess of labeled probe oligonucleotide (which binds specifically to either the mutant or the wild-type gene) is combined with the target nucleic acid under stringent hybridization conditions such that only exactly complementary strands will hybridize to any measurable extent. An enzyme is added which will cleave the probe when it is part of a duplex, but not in single stranded form. The mixture is then cycled through multiple cycles of annealing/enzyme digestion and denaturation. If the probe binds to the target, the result is the production of many small labeled probe-fragments, and the concurrent reduction in the number of full-size labeled probes. Either the increase in the number of fragments or the decrease in the number of full-sized probes can be detected and provides an amplified indication of the presence or absence of the target sequence in the sample.

An example of an enzyme which can be used in the catalytic hybridization amplification system is RNaseH which is used in combination with RNA probes; which are selectively cleaved when hybridized to a strand of target DNA. Restriction endonucleases which do not cleave phosphorothioate-modified DNA may also be used, provided that the target DNA is first copied to produce a phosphorothioate-modified target. Because this method combines both amplification and detection, prior amplification of the genomic DNA from the sample is generally not necessary.

Another technique useful in the present invention which combines amplification and detection relies on the autocatalytic replication of certain RNA's as described in U.S. Pat. No. 4,957,858, which is incorporated herein by reference. Briefly, in this technique a replicative RNA segment is ligated to a sequence specific oligonucleotide probe which binds to either the mutant or the wild-type form of the Asn291Ser mutation site in exon 6 of the LPL gene. This ligated probe is then combined with the genomic DNA in such a manner that the probe will bind if the matching sequence is present in the genomic DNA, and so that unbound probe can be separated from bound probe. For example, the genomic DNA may be immobilized on a solid support to facilitate washing out of unbound probe molecules. Thereafter, the RNA portion of the ligated probe is amplified, for example using the enzyme Q-beta replicase.

Yet another form of combination amplification/detection technique which is useful in the present invention is described in U.S. Pat. No. 5,124,246 which is incorporated herein by reference. In this technique, a total of five types of oligonucleotide probes are used. The first type of probe is a multimer oligonucleotide having a "star" type configuration with many generally identical arms. The second type of probe is a labeling probe. The labeling probe is complementary to the sequence of one of the arms of the multimer probe and includes a detectable label. The third type of probe is an immobilized probe. A plurality of this third type of probe is affixed to a solid support. The specific sequences used in these first three types of probes are independent of the nature of DNA being analyzed, except that they should not hybridize with this DNA directly.

The fourth type of probe is referred to as an amplifier probe. These probes are synthesized in two parts, one which is complementary to a portion of the normal sequence of exon 6 of the LPL gene away from the Asn291Ser mutation site, and one which is complementary to an arm of the multimer probe. A plurality of different types of amplifier probes is formed. These various types of probes are complementary to different, non-overlapping portions of the sequence. The fifth type of probe is a capture probe. The capture probe is also formed in two parts: one which is complementary to the site of the Asn291Ser mutation and one which is complementary to the immobilized probe.

The assay is performed by combining denatured genomic DNA with the plurality of amplifier probes and capture probes under conditions permitting hybridization. The result is the binding of numerous amplifier probes to exon 6 of the LPL gene. The capture probe will only bind, however, if the corresponding mutant (or non-mutant, depending on the sequence of the probe) is present. Thereafter, the solid support having the third probe immobilized thereon is introduced. A solid support-immobilized probe-capture probe-genomic DNA-amplifier probe sandwich will form if DNA complementary to the capture probe is present. The support is then washed to remove unbound material, and the multimer probe is added. The multimer probe binds to the support via the amplification probe only if the sandwich was formed in the first place. The support is then washed and a labeling probe is added. The labeling probe will bind to all of the available arms of the multimer probe on the solid support, thus providing numerous detectable labels for each actual mutation site in the DNA sample.

In the foregoing discussion of amplification and detection techniques, there is frequent mention of labeled probes or labeled primers. For purposes of this application, the label applied to the primer may take any form, including but not limited to radiolabels; fluorescent or fluorogenic labels;

colored or chromogenic labels; chemically reactive labels such as biotin; enzyme-labels, for example phosphatase, galactosidase or glucosidase enzymes which can produce colored or fluorescent reaction product in combination with substrates such as p-nitrophenyl phosphate (colored reaction product) or 4-methyl umbelliferyl phosphate (fluorescent cleavage product); and chemiluminescent labels.

A further aspect of the present invention is the particular oligonucleotide probes which may be used in one Or several of the techniques as discussed above for detection of the Asn291Ser mutation. Thus, for use in the case of mismatch primer amplification followed by RFLP analysis there is provided an oligonucleotide primer which binds specifically to a gene encoding for human lipoprotein lipase in a region adjacent to, but not overlapping the second base in the codon corresponding to residue 291 in human lipoprotein lipase, and which includes a mismatched base which does not correspond to the normal sequence of human lipoprotein lipase, whereby upon extension of the primer, using a target human lipoprotein lipase gene as a template, an extension product is produced which contains a restriction site which can be cleaved by a restriction endonuclease when the lipoprotein lipase product made by the target gene has a serine residue as amino acid 291, and does not contain such a restriction site when the lipoprotein lipase product made by the target gene has an asparagine residue as amino acid 291. A preferred primer which binds to the coding strand is one in which a base complementary to base number 1130 is changed from the normal thymine to guanine. For the non-coding strand, the change is from adenine to cytosine. A particularly preferred mismatch primer for binding to the coding strand has the sequence

CTGCTTCTTT TGGCTCTGAC TGTA             (SEQ 2).

For several of the detection methods discussed above, an oligonucleotide probe is utilized which binds to a site which includes the site of the specific mutation of interest. Thus, the present invention encompasses two types of oligonucleotide probes: (1) an oligonucleotide probe selected to bind specifically to a gene encoding a mutant human lipoprotein lipase having a serine residue as amino acid 291, wherein said probe binds to a portion of the gene including the bases coding for the serine residue; and (2) an oligonucleotide probe selected to bind specifically to a gene encoding a normal human lipoprotein lipase having a asparagine residue as amino acid 291, wherein said probe binds to a portion of the gene including the bases coding for the asparagine residue. These probes are preferably from 15 to 20 bases in length, and may be selected to bind to either the coding or the non-coding strand of the genomic DNA. Further, the probes will advantageously include a detectable label.

A further aspect of the present invention is a kit which may be used to detect the presence of the Asn291Ser mutation. The specific components of the kit will depend on the nature of the evaluation being conducted. In general, however, the kit will include a pair of primers selected to amplify a region of a human lipoprotein lipase gene encoding for amino acid 291 of human lipoprotein lipase. These primers may be primers for PCR, primers adapted for strand displacement amplification, or a normal primer and a mismatch primer. In addition, the kit may include oligonucleotide probes for use in the detection of the Asn291Ser mutation.

The discovery of the significance of the Asn291Ser mutation opens the door to the possibility of providing gene therapy to individuals having the mutation and thus to prevent or delay the onset of coronary artery disease and particularly premature atherosclerosis. In addition, since gene therapy to correct this defect would provide a patient with a fully functional lipoprotein lipase enzyme, therapeutic agents and methods used for this purpose may also be used effectively for other conditions associated with LPL mutations. Such conditions include infantile failure to thrive, hepatosplenomegaly, eruptive xanthomas, chronic and/or episodic abdominal pain, pancreatitis and lactescent plasma due to an accumulation of chylomicrons and very low density lipoproteins or their remnants in the plasma.

Gene therapy to introduce functional LPL may reduce the clinical manifestations stemming from hypertriglyceridemia in both LPL deficient homozygotes and heterozygotes. This gene transfer can be accomplished using adenovirus-DNA-polylysine conjugates; adenovirus constructs in which the normal LPL gene is inserted into the viral genome; or retroviral constructs in which the normal LPL gene is inserted into the viral genome. The vector may be introduced directly, for example by parenteral injection into the patient, or may be introduced via an implanted pseudo-organ.

Figure 4:
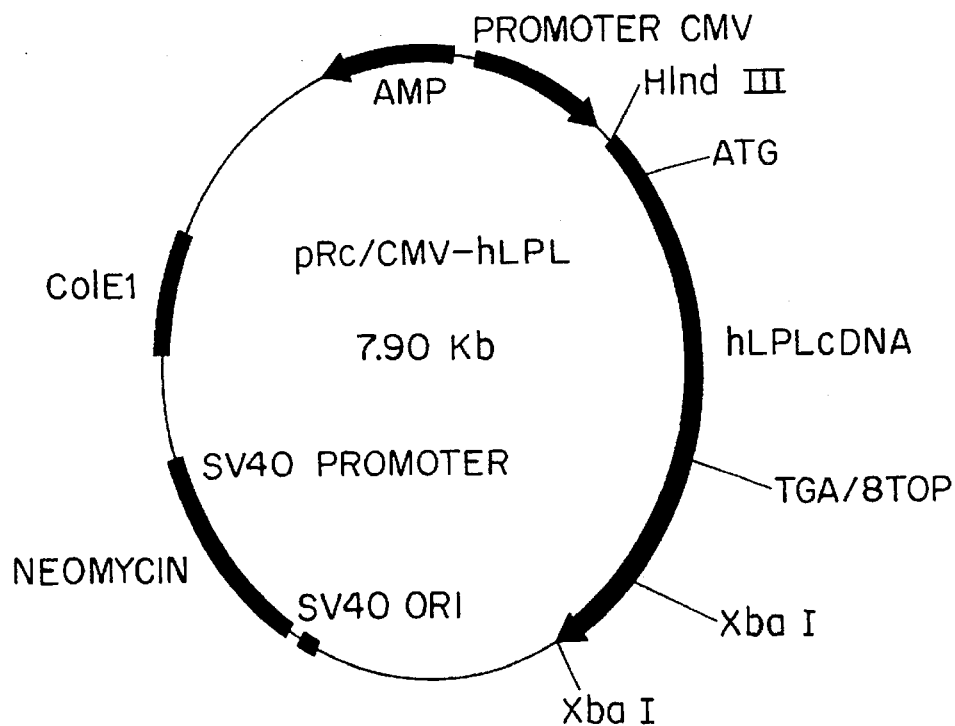
FIG. 4 shows a plasmid construct useful in accordance with the present invention.

FIG. 4 shows a plasmid construct useful in accordance with the present invention. As shown, the plasmid pRc/CMV-hLPL is 7.90 Kbases in size. The preparation of this particular plasmid is described below in Example 2. It will be appreciated by persons skilled in the art, however, that variations in this technique, or the precise structure of the plasmid may be made without departing from the present invention provided that the plasmid contains a functional h-LPL gene and an appropriate promoter. For example, tissue-specific promoters, particularly adipose tissue specific or muscle specific promoters might be used in place of the CMV promoter. Furthermore, while the SV40 promoter and the antibiotic resistance markers are convenient for research purposes, they are not necessary for therapeutic purposes.

To prepare a plasmid for transfection into mammalian, and particularly human cells, the plasmid is complexed with an adenovirus-polylysine conjugate. In general this process involves the harvesting and purification of a suitable adenovirus, for example a virus which is incompetent as a result of an E1A or an E3 deletion mutation. The purified virus is then conjugated with a polycationic material for associating with DNA such as polylysine, polyarginine or protamine, for example using a bifunctional reagent such as ethyl-3,3-dimethyl aminopropyl carbodimide (EDC) as a crosslinking agent. When the resulting adenovirus-polylysine conjugate is combined with a plasmid containing a normal LPL gene, an adenovirus-DNA-polylysine complex forms spontaneously. This complex transfects mammalian cells of various types when placed in media with the cells with relatively high efficiency, and the transfected cells produce functional LPL.

Mammalian cells may also be transduced (or transfected) using an adenovirus into which a gene encoding for normal LPL has been inserted. Preferred adenoviruses are those with an E1 or an E3 deletion mutation rendering the virus incompetent. The h-LPL gene can be conveniently inserted into the virus at the site of the deletion.

Specific modified adenoviruses useful in the present technique are based on the RSV β-Gal adenovector described by Strafford-Perricaudet et al., *J. Clin. Invest.*, 90: 626–630 (1992). This adenovector is based on adenovirus Ad5. Human LPL cDNA is introduced into the vector by homologous recombination using a modified form of Strafford-Perricaudet's pLTRβGalpIX plasmid. The plasmid contains an RSV LTR promoter or a CMV plus intron promoter, human LPL cDNA, a poly A site plus small intron from SV40 derived from a pSV2 vector. Mulligan et al., *Science*

209: 1422–1427 (1980) which are inserted between nucleotides 455 to 3329 of an Ad5 DNA which is also deleted in the E3 region. This results in the deletion of E1A and part of E1B, but, leaves pIX intact. The resulting adenoviruses are non-replicating but can be propagated in 293 cells which transcomplements the E1A activity.

A third type of vector which may be used to transduce (or transfect) mammalian cells is a retroviral vector. Suitable vectors include myeloproliferative sarcoma virus (MPSV)-based retroviral vectors into which human LPL cDNA is inserted under the transcriptional control of the constitutive enhancer-promoter regulatory elements of the MPSV long terminal repeat (LTR).

Gene transfer vectors can be introduced into a human subject either in vivo or ex vivo. In the case of an in vivo treatment, the gene transfer vector may be simply injected into the patient, for example parenterally, and allowed to find suitable target cells. In the case of ex vivo treatment, cells are grown in vitro and transduced or transfected with the virus, embedded in a carrier such as a collagen matrix, which is then implanted in the patient, for example as a subcutaneous implant. Preferred cells for use in ex vivo applications are fibroblast cells taken from the patient who will receive the implant.

EXAMPLE 1

The significance of the mutation resulting in a serine in place of an asparagine as amino acid 291 in human lipoprotein lipase (the "Asn291Ser mutation") was discovered as a result of a case controlled study of a large homogeneous sample of patients undergoing diagnostic coronary angiography. A total of 807 men, all of whom were of Dutch descent and had angiographically proven atherosclerosis with more than 50% stenosis of at least one major coronary vessel were included in the study. All of the patients were less than 70 years of age, and had total cholesterol levels between 4 and 8 mmol/l and triglyceride levels which did not exceed 4 mmol/l.

The control group for the study included 157 persons who did not have any history of angina or premature atherosclerosis, and who exhibited no signs of vascular disease upon physical examination. The controls were all less than 60 years of age and had baseline HDL levels greater than 0.95 mmol/l and triglyceride levels of less than 2.3 mmol/l.

DNA was extracted from leukocytes using a salt-chloroform extraction method as described in *Trends in Genetics* 5: 391 (1989). Exon 6 of the LPL gene was amplified with a 5'-PCR primer located in intron 5 near the 5' boundary of exon 6 having the sequence

GCCGAGATAC AATCTTGGTG                (SEQ 1)

and a 3' mismatch primer which was located in exon 6 near the Asn291Ser mutation. The mismatch primer had the sequence

CTGCTTCTTT TGGCTCTGAC TGTA           (SEQ 2).

PCR amplification reactions were performed using 0.5 µg of genomic DNA in BRL PCR buffer containing 1.5 mM MgCl$_2$, 200 µM dNTPS, 1 µM each primer and 2.5 units Taq polymerase (BRL). The reaction mixture was denatured at 95° C. for 1 minute, annealed at 51° C. for 1 minute and extended at 72° C. for 45 seconds for a total of 35 cycles. Twenty µl of the PCR product was then digested with 10 units RsaI enzyme, 3.5 µl of 10× reaction buffer 1 (BRL), and 9.5 µl of water at 37° C. for 2 hours. The digested fragments were then separated on 2% agarose gel.

Because the combination of the mismatch primer and the Asn291Ser mutation produces an RsaI restriction site which is absent when the mismatch primer is used to amplify the wild-type gene, the restriction fragments observed on the agarose gel were different when the mutation was present. Using this difference as a diagnostic indicator, it was determined that the Asn291Ser mutation was seen in 41 of the 807 or 5.09% of the patients in the test group, but in only 3 out of 157 or 1.9% of the patients in the control group. When a subgroup of the 494 patients in the test group with hypoalphalipoproteinemia was considered, it was found that a higher percentage of these patients, i.e., 6.9% (34 out of 494) had the Asn291Ser mutation. When a further subgroup of the test group was considered by selecting those individuals with low HDL-C levels (<1.0%), and excluding those individuals who had blood glucose >6.8 mmol/l (suggestive of diabetes) and those on β-blocker therapy, 11.3% (12 out of 106 patients) had the mutation. This proportion further increased when those with still lower HDL-C levels were considered separately. Thus, among persons with HDL-C levels less than 0.9 mmol/l, 8 out of 68 or 12.5% had the Asn291Ser mutation, while among those with HDL-C levels less than 0.8 mmol/l, 5 out of 32 or 15.6% had the Asn291Ser mutation.

EXAMPLE 2 pRc/CMV vector (Invitrogen) was linearized using XbaI and Hind III. An XbaI/HindIII fragment containing h-LPL cDNA having a length of about 2.4 kb was inserted into the vector. DH5-alpha was transformed with the construct. Transformed cells were selected from agar plates based upon ampicillin resistance, and grown in LB medium. The plasmid construct, pRc/CMV-hLPL which is shown in FIG. 4, was isolated from the cultures by alkaline lysis and CsCl centrifugation.

EXAMPLE 3

A purified preparation of an incompetent adenovirus (E1A deletion mutant) was prepared by growing 293 cells in 2 liter spinner flasks to a cell density of 4.5×10$^6$/ml and infecting the cells with DL312 adenovirus stock at MOI (multiplicity of infection) 20–50 for 1 hour. Forty hours post infection, the cells were harvested by centrifugation. A lysate was prepared by subjecting the harvested cells to 3 freeze/thaw cycles. This lysate was centrifuged in a two-layer CsCl gradient (d=1.25, d=1.4) in a Beckman SW41 swing rotor at 35,000 rpm and 18° C. for 90 minutes. After the ultracentrifugation, the virus was recovered from the interface between the two CsCl layers using a syringe and a long needle. The recovered virus was then placed onto a CsCl solution (d=1.34) and centrifuged for 16 hours at 35,000 rpm and 18° C. After this centrifugation, the virus was again recovered from the interface and was then dialyzed three times (1 hour per cycle) against a sterile buffer (Tris 10 mM, MgCl$_2$ 1 mM, NaCl 0.135M). In the third dialysis cycle, the buffer included 10% glycerol to enhance storage stability. The purified virus was kept frozen at −80° C. until ready to use.

EXAMPLE 4

Virus prepared as described in Example 3 was mixed with polylysine (10 mM) and EDC (2 mM) for 4 hours at 4° C. in HBS/buffered saline to form adenovirus-polylysine conjugates. The conjugates were re-isolated by CsCl gradient centrifugation using the same protocol as the final centrifugation in Example 3.

The re-isolated conjugates ($5 \times 10^9$/ml) were incubated with 60–70% confluent Chinese Hamster Ovary cells (CHO K-1) in 2% FBS medium (1 ml) and 6 µg of the plasmid pRc/CMV-hLPL. As a control to assess the extent to which transfection occurred, a second set of samples was prepared in the same manner using the plasmid pRc/CMV-B-gal which includes a gene encoding β-galactosidase in place of h-LPL. After two hours, the medium containing the conjugates was aspirated out, and new medium (10% FBS) was added to the cells.

By incubating the control cells infected with pRc/CMV-B-gal in the presence of X-gal, and counting the number of cells which evidenced the characteristic blue color which result from cleavage of X-gal by β-galactosidase, it was determined that the transfection efficiency in this system varied from 2% when the virus solution was diluted 2000× to 50% when the virus solution was diluted 125×. Thus, 50% transfection efficiency could be achieved in vitro at titers of $0.5-1 \times 10^8$, which is at least 10-fold less than the titers which would normally be used in vivo.

To determine the expression of LPL in cells transfected with pRc/CMV-LPL, the activity of LPL was determined and compared to the activity observed for control cells transfected with pRc/CMV-B-gal. For the control cells, the activity measured was 12 mU/ml. For the cells transfected with pRc/CMV-LPL, the activity measured was 20 mU/ml.

EXAMPLE 5

The experiments described in Example 5 were repeated, except that the cells used were LPL-deficient cat fibroblast cells or HepG-2 liver cells. Table 1 shows the infection efficiencies at various virus dilutions which were determined for these cell types as well as the CHO K-1 cells.

TABLE 1

| | DILUTION | | | | |
|---|---|---|---|---|---|
| VIRUS | 2000× | 1000× | 500× | 250× | 125× |
| CHO K-1 | 2 | 5 | 15 | 30 | 50 |
| Cat Fibroblast | 10 | 20 | 50 | 100 | 100 |
| HepG-2 | 20 | 50 | 100 | 100 | 100 |

Table 2 shows the LPL activity measured for Cat fibroblast cells, and the LPL mass measured for cat fibroblast cells and HepG-2 cells. In addition, Table 2 shows positive control results for COS EV101 cells which are over producers of LPL. It can be seen from this data that there is a substantial increase in the plasmid activity and also in the amount of the active dimer form of the enzyme.

TABLE 2

| | | LPL Activity | LPL MASS (ng/ml) | | |
|---|---|---|---|---|---|
| Cell Type | plasmid | (mU/ml) | total | monomer | dimer |
| CHO K-1 | control | 12 | n.d. | n.d. | n.d. |
| | pRc/CMV-LPL | 20 | n.d. | n.d. | n.d. |
| Cat Fibroblasts | control | 0.15 | 26 | 24 | 2 |
| | pRc/CMV-LPL | 1.5 | 128 | 88 | 34 |

TABLE 2-continued

| | | LPL Activity | LPL MASS (ng/ml) | | |
|---|---|---|---|---|---|
| Cell Type | plasmid | (mU/ml) | total | monomer | dimer |
| HepG-2 | control | n.d. | 33 | 28 | 6 |
| | pRc/CMV-LPL | n.d. | 164 | 113 | 51.5 |
| COS | EV101 | 50 | 530 | 87 | 443 |

EXAMPLE 6

Vectors for introducing human LDL cDNA into mammalian cells were made using the murine leukemia retroviral backbones M3neo, M5neo and JZen1 which contain long terminal repeat (LTR) regulatory sequences for the myeloproliferative sarcoma virus. To generate the vectors M3neoLPL and M5neoLPL, a 1.56 kb DraI-EcoRI fragment encompassing the entire LPL amino acid coding region was subcloned into a unique BamHI site located 3' or 5' to the neomycin phosphotransferase ($neo^r$), respectively. Expression of both genes is LTR driven in these vectors; in M3neoLPL, functional LPL message would derive from the spliced proviral transcripts whereas for M5neoLPL, LPL message would derive from the full length unspliced proviral transcript. To construct JZenLPLtkneo, a 1092 bp Xho I/SalI fragment for $neo^r$ was isolated from pMCIneo and inserted into the SalI site of the plasmid pTZ19R, containing the herpes simplex virus thymidine kinase (tk) promoter. The SmaI/HindIII tkneo fragment from the pTZ19R was inserted into the Hpa I/Hind III site of JZen1. A 1.56 kb human LPL cDNA sub-fragment was then cloned in the BamHI site of JZentkneo. Human LPL cDNA was also subcloned directly into JZen1 to construct JZenLPL.

Virus producer cells lines were then made for each of the viral constructs using the amphotropic retroviral packaging cell line GP-Am12 and the ecotropic packaging line GP-E86. Both cell lines were cultured in HXM medium, which is Dulbecco's modified Eagle's medium (DME) supplemented with 10% heat-inactivated (55° C. for 20 minutes) newborn calf serum (Gibco-BRL), hypoxanthine (15 µg/ml), xanthine (250 µg/ml) and mycophenolic acid (25 µg/ml). For GP-AM12 cells, hygromycin B (200 µg/ml) was also added to the HXM medium. All cells were cultured at 37° C. in a humidified atmosphere of 5% $CO_2$.

EXAMPLE 7

A variety of hematopoietic cell lines were tested using the neomycin resistance marker incorporated in the vector to determine whether transduction occurred as a result of coincubation with M3neoLPL in vitro. K562 erythroid cells, HL60 myeloid cells, and U937 and THP-1 monocytic cells obtained from the American Type Culture Collection were grown in RPMI 1640 medium containing 10% fetal bovine serum. The cells were then infected by cocultivation (24–48 hours) with irradiated (15 Gy x-ray) near confluent producer cells with polybrene 4 µg/ml added to the co-cultivation medium (RPMI/10% fetal bovine serum). After the infection period, the hematopoietic target cells were maintained in suspension culture for 24 hours before selection in 1 mg/ml G418. The gene transfer efficiencies observed are summarized in Table 3.

The mass of LPL produced was determined for each of the transduced hematopoietic cells lines using two ELISAs. The antibodies used were MAb 5D2 which binds to the bioactive dimeric form of LPL and MAb 5F9 which binds to both the bioactive dimer and the inactive monomeric form of LPL. The results are summarized in Table 3.

Finally media supernatants were measured for LPL bioactivity. The results of this study are also reported in Table 3.

TABLE 3

| Cell Line | Gene Transfer Efficiency | Increase in Bioactivity | Increase in LPL Dimer |
|---|---|---|---|
| K562 | 57% | 11-fold | 5-fold |
| HL60 | 47% | 9-fold | 3-fold |
| U937 | 45% | 14-fold | 54-fold |
| THP-1 | 41% | 4-fold | 2-fold |

These results demonstrate that for each cell type, good transduction efficiencies were achieved, and production of functional LPL resulted.

Transduced HL60 and THP-01 cells were differentiated in macrophages by exposing the cells to 10ng/ml of phorbal ester, PdBU (Phorbol 12,13-dibutyrate) for 5 days. For HL60 cells, the LPL bioactivity increased a further 1.8-fold, while the amount of LPL dimer increased another 1.8-fold. No further increase was observed upon differentiation of THP-1 cells.

EXAMPLE 8

NIH 3T3 murine fibroblasts were grown in DME medium containing 10% (vol/vol) fetal bovine serum. The medium on near confluent 60 mm tissue culture plates of viral producer cells 24 hours prior to the planned infection with 10 ml DME/10% newborn calf serum. This medium was removed at the time of infection, concentrated 10-fold to a 1.0 ml final volume by filter centrifugation in Centriprep-30 tubes (Amicon) and diluted 1:4 with DME/10% fetal bovine serum with 4 µg/ml polybrene added. Fibroblasts were added to this preparation and incubated for 24–48 hours at 37° C. 24 hours after viral exposure, cells were subjected to selection in 1.0 mg/ml G418 and grown to confluence. Testing for LPL production revealed a 16-fold increase in total LPL production above constitutive levels which consisted almost entirely of dimeric protein, and a 10-fold increase in secreted LPL bioactivity.

EXAMPLE 9

The experiment of Example 8 was repeated using primary human fibroblast cells, FC 1898 and FC 1901 from diagnostic skin biopsies. No measurable levels of endogenous LPL protein mass or bioactivity could be detected prior to retroviral-mediated LPL gene delivery. Post transduction levels of total LPL mass were massively elevated at least 400 times above normal. However, at least 82% of this exogenous LPL protein was of the inactive monomeric form. At least a 52-fold (74.8±22/9) increase in dimeric LPL production was seen with significantly elevated secretion of bioactive LPL, approximately 24 times higher (26.9±3.0) than background LPL levels.

We claim:

1. A method for evaluating susceptibility of a human individual to premature atherosclerosis comprising the steps of:

(a) obtaining a sample of DNA from the individual; and (b) evaluating the sample of DNA for the presence of nucleotides encoding a serine residue at amino acid 291 of the lipoprotein lipase gene product, wherein the presence of a serine residue is indicative of increased susceptibility to premature atherosclerosis.

2. A method according to claim 1, wherein the sample is amplified using a mismatched primer to form an amplified product, and the evaluation of step (b) is performed on the amplified product which is evaluated for a restriction fragment length polymorphism.

3. A method according to claim 2, wherein the mismatched primer binds to the coding strand of the human lipoprotein lipase gene and wherein the base complementary to base number 1130 in the coding strand is changed from the normal thymine to guanine.

4. A method according to claim 2, wherein the mismatched primer binds to the non-coding strand of the human lipoprotein lipase gene and wherein the base complementary to base number 1130 in the non-coding strand is changed from the normal adenine to cytosine.

5. A method according to claim 2, wherein the mismatched primer has the sequence

CTGCTTCTTT TGGCTCTGAC TGTA (SEQ 2).

6. A method according to claim 1, wherein the sample is amplified to increase the amount of genetic material encoding for amino acid 291 of human lipoprotein lipase prior to evaluating the sample for the presence of nucleotides encoding a serine residue at amino acid 291.

7. A method according to claim 6, wherein the sample is amplified by a polymerase chain reaction.

8. A method according to claim 6, wherein the sample is amplified by strand displacement amplification.

9. A method according to claim 6, wherein the amplified sample is evaluated for the presence of nucleotides encoding a serine residue at amino acid 291 by combining the sample with a sequence specific oligonucleotide probe which is complementary to a region including the nucleotides encoding amino acid 291 of the lipoprotein lipase gene product when amino acid 291 is serine, and wherein the formation of a DNA duplex between the probe and the amplified sample is determined.

10. A method according to claim 6, wherein the amplified sample is evaluated for the presence of nucleotides encoding a serine residue at amino acid 291 by combining the sample with a sequence specific oligonucleotide probe which is complementary to a region including the nucleotides encoding amino acid 291 of the lipoprotein lipase gene product when amino acid 291 is asparagine, and wherein the formation of a DNA duplex between the probe and the amplified sample is determined.

11. A method according to claim 1, wherein the sample is evaluated for the presence of nucleotides encoding a serine residue at amino acid 291 by combining the sample with a sequence specific oligonucleotide probe which is complementary to a region including the nucleotides encoding amino acid 291 of the lipoprotein lipase gene product when amino acid 291 is serine, and wherein the formation of a DNA duplex between the probe and genetic material in the sample is determined.

12. A method according to claim 1, wherein the sample is evaluated for the presence of nucleotides encoding a serine residue at amino acid 291 by combining the sample with a sequence specific oligonucleotide probe which is complementary to a region including the nucleotides encoding amino acid 291 of the lipoprotein lipase gene product when amino acid 291 is asparagine, and wherein the formation of a DNA duplex between the probe and genetic material in the sample is determined.

13. A method for evaluating the causation of premature atherosclerosis in a human patient diagnosed as having premature atherosclerosis, comprising the steps of:
(a) obtaining a sample of DNA from the individual; and
(b) evaluating the sample of DNA for the presence of nucleotides encoding a serine residue at amino acid 291 of the lipoprotein lipase gene product, wherein the presence of a serine residue is indicative of increased susceptibility to premature atherosclerosis.

14. A method for evaluating a human individual for risk of coronary artery disease, comprising the steps of
(a) obtaining a sample of DNA from the individual; and
(b) evaluating the sample of DNA for the presence of a serine residue at amino acid 291 of the lipoprotein lipase gene, wherein the presence of a serine residue is indicative of increased risk of coronary artery disease.

15. A kit for evaluating the susceptibility of a human individual to premature atherosclerosis, comprising in packaged combination a pair of primers selected to amplify a region of a human lipoprotein lipase gene encoding for amino acid 291 of human lipoprotein lipase, wherein one primer of the pair of primers is a mismatch primer effective in combination with the bases encoding amino acid 291 to introduce a restriction site into the amplified lipoprotein lipase gene, said restriction site being differentially present in amplified normal lipoprotein lipase genes and in amplified lipoprotein lipase genes which have a mutation in the bases encoding amino acid 291.

16. A kit according to claim 15, wherein the mismatch primer binds to the coding strand of the human lipoprotein lipase gene and wherein the base complementary to base number 1130 in the coding strand is changed from the normal thymine to guanine.

17. A kit according to claim 16, further comprising a container of the restriction endonuclease RsaI.

18. A kit according to claim 15, wherein the mismatch primer binds to the non-coding strand of the human lipoprotein lipase gene and wherein the base complementary to base number 1130 of the non-coding strand is changed from the normal adenine to cytosine.

19. A kit according to claim 18, further comprising a container of the restriction endonuclease RsaI.

20. A kit according to claim 14, wherein the mismatch primer has the sequence

CTGCTTCTTT TGGCTCTGAC TGTA (SEQ 2).

21. A kit for evaluating the susceptibility of a human individual to premature atherosclerosis comprising in packaged combination a pair of primers selected to amplify a region of a human lipoprotein lipase gene encoding for amino acid 291 of human lipoprotein lipase and an oligonucleotide probe selected to bind specifically to a portion of the gene encoding human lipoprotein lipase gene, wherein said probe binds to a portion of the gene including the bases coding for amino acid 291.

22. A kit according to claim 21, wherein the oligonucleotide probe is selected to bind specifically to a gene encoding mutant human lipoprotein lipase gene having a serine as amino acid 291, wherein said probe binds to a portion of the gene including the bases coding for the serine at amino acid 291.

23. A kit according to claim 22, wherein the primer pair is adapted for use in a strand displacement amplification technique.

24. A kit according to claim 21, wherein the oligonucleotide probe is selected to bind specifically to a gene encoding a normal human lipoprotein lipase gene having an asparagine as amino acid 291, wherein said probe binds to a portion of the gene including the bases coding for the asparagine at amino acid 291.

25. A kit for evaluating the susceptibility of a human individual to premature atherosclerosis or risk, comprising in packaged combination a pair of primers selected to amplify a region of a human lipoprotein lipase gene encoding for amino acid 291 of human lipoprotein lipase wherein one of the primers is selected to bind to a region of the human lipoprotein lipase gene which includes the bases encoding for amino acid 291.

26. A kit according to claim 25, wherein the primer which binds to the region of the human lipoprotein gene which include the bases encoding for amino acid 291 is complementary to a sequence which encodes for serine as amino acid 291.

27. A kit according to claim 25, wherein the primer which binds to the region of the human lipoprotein gene which include the bases encoding for amino acid 291 is complementary to a sequence which encodes for asparagine as amino acid 291.

28. A kit for evaluating the susceptibility of a human individual to premature atherosclerosis, comprising in packaged combination a primer adapted for strand displacement amplification of a region of a human lipoprotein lipase gene encoding for amino acid 291 of human lipoprotein lipase, and an oligonucleotide probe having a detectable label attached thereto, said oligonucleotide probe being selected to bind specifically to the region of a human lipoprotein lipase gene encoding for amino acid 291 of human lipoprotein lipase.

29. A kit according to claim 28, wherein the oligonucleotide probe is selected to bind specifically to DNA encoding for serine as amino acid 291.

30. A kit according to claim 28, wherein the oligonucleotide probe is selected to bind specifically to DNA encoding for asparagine as amino acid 291.

31. A kit for evaluating a human individual for risk of coronary artery disease, comprising in packaged combination a pair of primers selected to amplify a region of a human lipoprotein lipase gene encoding for amino acid 291 of human lipoprotein lipase, wherein one primer of the pair of primers is a mismatch primer effective in combination with the bases encoding amino acid 291 to introduce a restriction site into the amplified lipoprotein lipase gene, said restriction site being differentially present in amplified normal lipoprotein lipase genes and in amplified lipoprotein lipase genes which have a mutation in the bases encoding amino acid 291.

32. An oligonucleotide probe selected to bind specifically to a gene encoding a mutant human lipoprotein lipase having a serine residue as amino acid 291, wherein said probe binds to a portion of the gene including the bases coding for the serine residue.

33. An oligonucleotide probe according to claim 32, further comprising a detectable label.

34. An oligonucleotide probe selected to bind specifically to a gene encoding a normal human lipoprotein lipase having an asparagine residue as amino acid 291, wherein said probe binds to a portion of the gene including the bases coding for the asparagine residue.

35. An oligonucleotide probe according to claim 34, further comprising a detectable label.

36. An oligonucleotide primer which binds specifically to a gene encoding for human lipoprotein lipase in a region adjacent to, but not overlapping the second base in the codon corresponding the residue 291 in human lipoprotein lipase, said primer including a mismatched base which does not correspond to the normal sequence of human lipoprotein lipase, whereby upon extension of the primer using a target human lipoprotein lipase gene as a template an extension product is produced which contains a restriction site which can be cleaved by a restriction endonuclease when the lipoprotein lipase product made by the target gene has a serine residue as amino acid 291, and does not contain such a restriction site when the lipoprotein lipase product made by the target gene has an asparagine residue as amino acid 291.

37. A primer according to claim 36, wherein the primer binds to the coding strand of the human lipoprotein lipase gene and wherein the base complementary to base number 1130 of the coding strand is changed from the normal thymine to guanine.

38. A primer according to claim 36, wherein the primer binds to the non-coding strand of the human lipoprotein lipase gene and wherein the base complementary to base number 1130 of the non-coding strand is changed from the normal adenine to cytosine.

39. A primer according to claim 36, wherein the primer has the sequence

CTGCTTCTTT TGGCTCTGAC TGTA          (SEQ 2).

\* \* \* \* \*